United States Patent [19]

Magnussen, Jr. et al.

[11] 4,389,163
[45] Jun. 21, 1983

[54] PRESSURE BOOSTER SYSTEM FOR FLUIDS

[75] Inventors: Haakon T. Magnussen, Jr., Pinole; Stephen J. Ruskewicz, Kensington, both of Calif.

[73] Assignee: Altex Scientific, Inc., Berkeley, Calif.

[21] Appl. No.: 275,556

[22] Filed: Jun. 19, 1981

Related U.S. Application Data

[63] Continuation of Ser. No. 425, Jan. 2, 1979, abandoned.

[51] Int. Cl.³ .................. F04B 41/02; F04B 49/06; F04B 49/00; F04B 3/00
[52] U.S. Cl. .................................. 417/2; 417/43; 417/265; 417/385
[58] Field of Search .................... 417/2, 43, 244, 265, 417/385

[56] References Cited

U.S. PATENT DOCUMENTS

| 1,818,413 | 8/1931 | Luitweiler | 417/534 |
|---|---|---|---|
| 3,256,824 | 6/1966 | Sobardt | 417/385 |
| 3,551,076 | 12/1970 | Wilson | 417/385 |
| 3,584,977 | 6/1971 | Coleman et al. | 417/2 |
| 3,817,658 | 6/1974 | Murase et al. | 417/2 |
| 4,003,679 | 1/1977 | McManigill | 417/246 |
| 4,028,018 | 7/1977 | Audsley | 417/534 |
| 4,072,210 | 2/1978 | Chion | 417/525 |
| 4,245,963 | 1/1981 | Hutchins et al. | 417/265 |

FOREIGN PATENT DOCUMENTS 623279  3/1927  France ................. 417/385

Primary Examiner—William L. Freeh
Attorney, Agent, or Firm—R. J. Steinmeyer; Robert R. Meads; John R. Shewmaker

[57] ABSTRACT

A pressure booster system for fluids using one or more injectors for delivering a relatively low pressure output flow of fluid. A fluid accumulator receives the output from one or more injectors. A detector reveals any fluid mass change in the accumulator in relation to a selected value of fluid mass. A relatively high pressure pump increases the pressure of the output flow from the accumulator in accordance with the change of fluid mass within the accumulator which results in high pressure metering.

17 Claims, 12 Drawing Figures

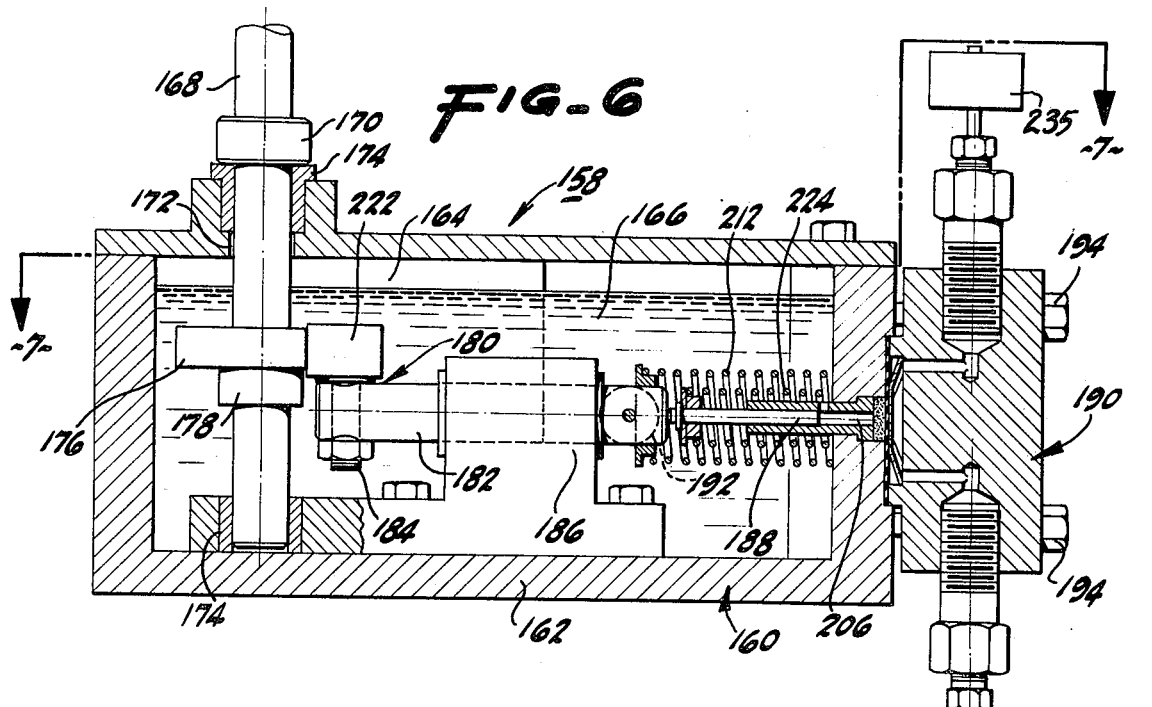
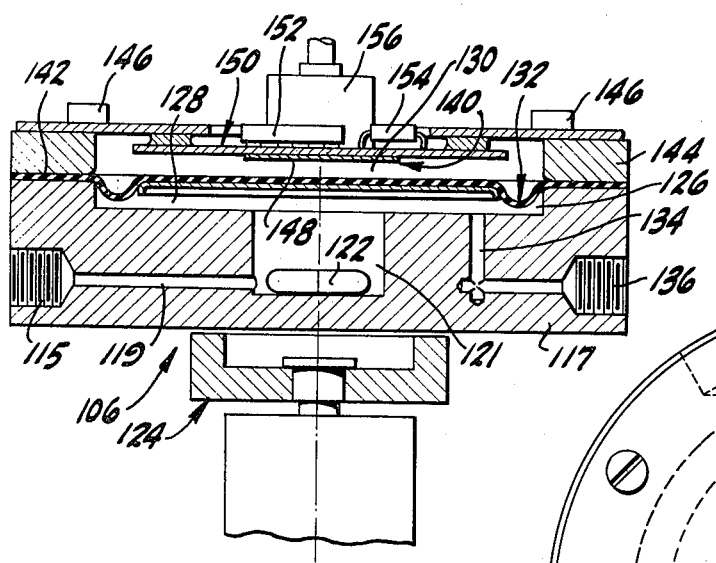
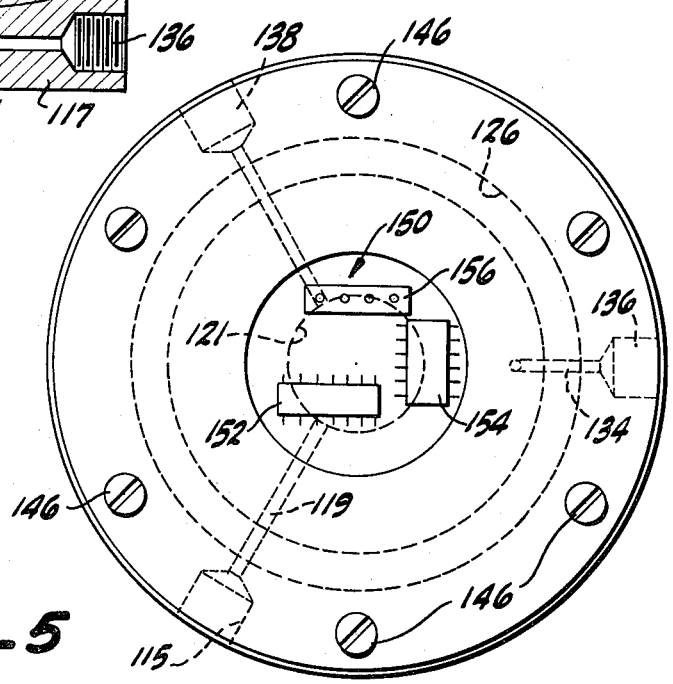

PRESSURE BOOSTER SYSTEM FOR FLUIDS

This is a continuation, division, of application Ser. No. 000,425, filed Jan. 2, 1979, now abandoned.

BACKGROUND OF THE INVENTION

The present invention relates to a pressure booster system for fluids. The system of the present invention defines particular application in the liquid chromatography field where it is necessary to deliver fluids at high pressure with a minimum of pulsation and at an accurate flow rate.

A typical liquid chromatography system employs a packed column to effect the separation of solute from a liquid sample. A detector analyzes the outflow from the column to identify particular components in the solute. Many chemical components exhibit similar elution characteristics and therefore exit the packed column at nearly the same time. Therefore, forcing the liquid sample through the column smoothly in a continuous and well defined flow rate is essential to the obtaining of accurate analyses. Prior liquid chromatography systems employ high pressure pumps, of the positive displacement type, to force the liquid sample through the packed column. Unfortunately, piston or piston-like pumps inherently produce an output flow having pulsations. High pressure piston pumps depend on proper operation of check valves for precise flow rate delivery. Although the use of dual piston pumps with overlapping cam characteristics have eliminated a portion of the flow pulsation, elaborate feedback controls are necessary to further reduce pulsations.

In this regard reference is made to U.S. Pat. No. 3,917,531 to Magnussen which describes a flow feedback system which employs a flow transducer to vary the motor speed of the pump according to a feedback signal. A solvent system described in U.S. Pat. No. 3,398,689 to Allington discloses a proportioning system for liquid chromatographic applications which utilize motor velocity feedback as a method of varying the pumping rate of the liquid. U.S. Pat. No. 3,932,078 to Ball et al employs a control means which measures the pressure during the pumping period of one piston and transforms the same into a pressure standard for a second piston, which operates under an overlapping cam arrangement.

All of the prior art systems require precision built high pressure metering pumps and feedback controls which must adjust for a multitude of corrections as an adjunct to liquid characteristics operating at high pressures. Prior art precision solvent metering pumps are expensive to construct and are markedly less reliable than other components of a liquid chromatographic system.

SUMMARY OF THE INVENTION

In accordance with the present invention a pressure booster system for fluids is provided. The system of the present invention employs a novel and original concept which externalizes in the system hereinafter described.

The system employs injector means which delivers a relatively low pressure output of fluid at a very accurate rate. The injector means operates at very low pressure and thus encounters few of the problems associated with high pressure metering pumps of the same genre. The injector means may take the form of a single pump or a multiplicity of pumps operating in collaboration to pump a single solution or a plurality of solutions.

The output of the injector means is fed into means for accumulating fluid mass. Such means may take the form of a fluid container having a flexible diaphragm portion. Thus an increase in the volume of fluid within the fluid accumulating means would push outwardly and move the diaphragm portion of the container in the same direction, and vice versa. The system also includes means for detecting a fluid mass change in the fluid mass accumulating means relative to a reference value of the fluid mass confined therein ie: volume, density, pressure, and the like.

The output flow from the fluid mass accumulating means travels to relatively high pressure pump means which in turn boosts the accurately metered inlet flow rate of fluid to a relatively high pressure outlet flow rate of fluid, retaining the accurately metered characteristic of the flow stream. The high pressure pump means is regulated by control means which derives the flow rate adjustments from the detection means which represents the difference between the mass in the fluid mass accumulating means and a reference value. Thus, the fluid mass accumulating means serves as a node in the mechanical and feedback control aspects of the system. The control means may employ an electrical, mechanical, pneumatic, and other known signal transmission media to effect the controlling function. It should be apparent that a novel and useful pressure booster system for fluids has been described which possesses many advantages not shown by the prior art.

It is therefore an object of the present invention to provide a pressure booster system for fluids which accurately delivers fluid at a high pressure and greatly eliminates pulsation inherent in positive displacement pumps.

It is another object of the present invention to provide a pressure booster system for fluids which utilizes low pressure injector means which delivers a very accurate and pulseless flow rate of fluid in combination with a high pressure booster pump and control means which employs a fluid mass accumulator to aid in the control of the high pressure output from the system.

It is yet another object of the present invention to provide a pressure booster system for fluids which automatically compensates for check valve leakage on the high pressure side of the system.

Another object of the present invention is to provide a pressure booster system for fluids which employs a low pressure metering pump which is simple and inexpensive to manufacture, operate, and maintain, and which is highly reliable.

Another object of the present invention is to provide a pressure booster system for fluids which employs a high pressure pump means which is delivered by injector means to the low pressure inlet of the high pressure pump means, thus, flow rate is defined at low pressure by the injector means rendering the high pressure pump means as a slave to the injector means.

Another object of the present invention is to provide a pressure booster system for fluids which requires only a single booster in multisolvent gradient systems and where that single booster has a very small hold-up volume minimizing the spreading of gradients formed at the inlet summing node and virtually eliminates cyclic variations found in prior art gradient systems.

A further object of the present invention is to provide a pressure booster system for fluids which employs injector means capable of producing a liquid chromatographic solvent gradient in combination with fluid mass accumulating means and a solitary high pressure slave pump.

Yet another object of the present invention is to provide a pressure booster system which delivers a precision flow of fluid without critical dependence on the operation of high pressure check valves.

Another object of the present invention is to provide a pressure booster system which utilizes in the low pressure section positive acting valves, thus eliminating check valves which are more prone to leakage.

Another object of the present invention is to provide injector means employing dual pump means with an overlapping cam drive which operates at relatively low pressure and thus virtually eliminates pulsations from the output flow therefrom.

The system possesses other objects and advantages especially as concerns particular features and characteristics thereof which will become apparent as the specification continues.

For a better understanding of the invention, reference is made to the following detailed description.

BRIEF DESCRIPTION OF THE DRAWINGS

FIG. 4 is a partially broken sectional view of the fluid mass accumulating means.

FIG. 5 is a top plan view of the fluid mass accumulating means.

FIG. 6 is a partially broken sectional view of the high pressure pump means.

Various aspects of the present invention will evolve from the following detailed description thereof which should be taken in conjunction with the heretofore described drawings.

DESCRIPTION OF THE PREFERRED EMBODIMENTS

Figure 1:
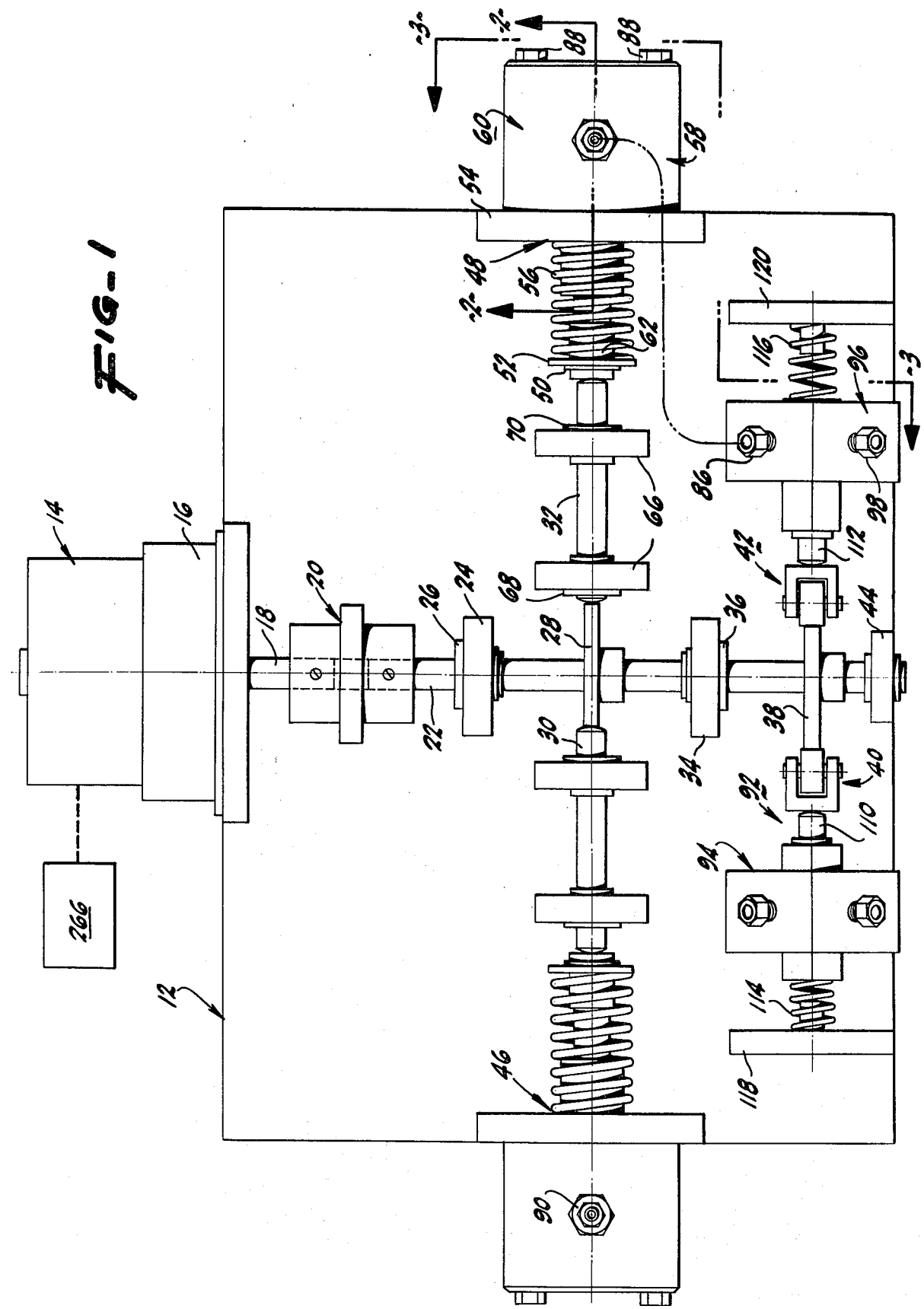
FIG. 1 is a top plan view of the injector means of the present invention.
Figure 10:
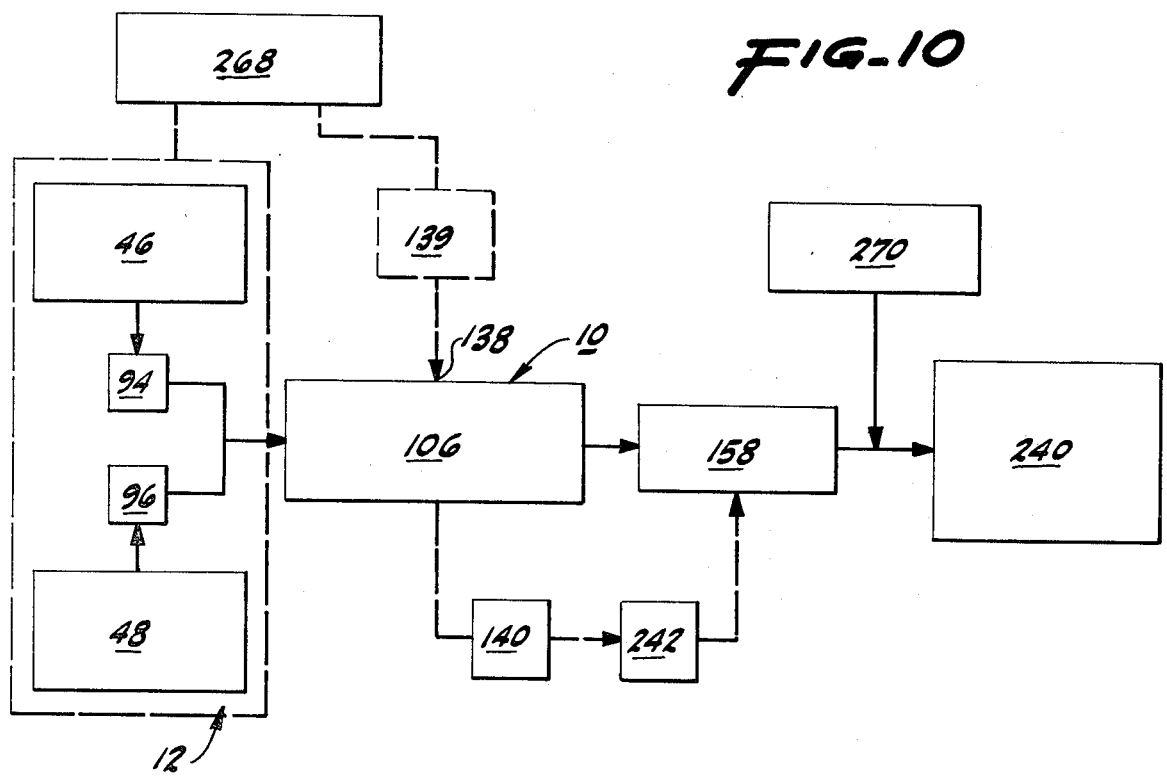
FIG. 10 is a block diagram of the overall pressure booster system for fluids.

The invention as a whole is shown in the drawings by reference character 10, FIG. 10. The system 10 includes as one of its elements injector means 12, FIG. 1, which is employed for the delivery of a solvent stream. Injector means 12 includes an electrical motor 14 which motivates a gear mechanism (not shown) within gear box 16. Electrical motor 14 turns shaft 18 at a predetermined shaft rotational speed. Coupling 20 connects shaft 18 to shaft 22 which turns at the same rate as shaft 18. Bearing 24 having flange 26 permits the extension of shaft 22 to cam 28. As shown in FIG. 1, cam 28 contacts cam followers 30 and 32. Shaft 22 extends through bearing 34 including flange 36. Cam 28 moves cam followers 40 and 42. Shaft 22 is finally supported by bearing 44 on the terminus thereof. The functioning of cam followers 30, 32, 40, and 42 will be explained hereinafter as the specification continues.

Figure 2:
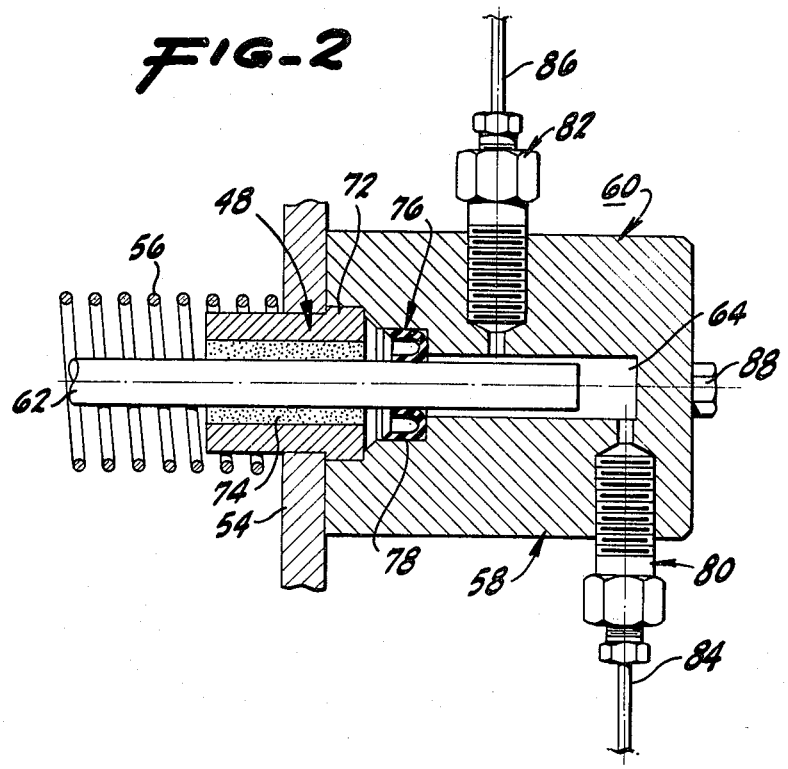
FIG. 2 is a sectional view taken along line 2—2 of FIG. 1.

Injector means 12 includes a first pump 46 and a second pump 48. With reference to FIG. 1 it may be apparent that cam 28 operates the pumping mechanism of pumps 46 and 48. FIG. 2 depicts pump 48 in detail. The components of pump 48 are virtually identical to the components for pump 46. Therefore the following description of pump 48 also applies to pump 46, shown in FIG. 1. Pump 48 includes the heretofore described cam follower 32. Washer 52 and plate 54 confine return spring 56 which functions to urge cam follower 32 against cam 28. End plate 54 forms one end of housing 58 for the liquid head portion 60 of pump 48. Washer 52 adjacent annular ring 50, and plate 54 offer a bearing surface to return spring 56. Cam follower 32 contacts piston 62 such that piston 62 reciprocates within a piston chamber 64. Cam follower 32 is supported by guide means 66 which includes bearings 68 and 70. Focussing attention on FIG. 2 it may be seen that piston 62 extends through bushing 72, held in place by plate 54. Bearing means 74 supports and guides piston 62 independently of cam follower 32. Bearing means 74 may be constructed of carbon such that piston 62 is lubricated thereby. Seal means 76, which may have an element 78 of cup shape configuration, effectively separates chamber 64 from leakage. Liquid head 60 includes inlet 80 and outlet 82. Inlet 80 and outlet 82 have no check valves normally associated with liquid chromatographic systems. Fastening means 88 holds housing 58 to plate 54, thus holding bushing 72 and seal means 76 in place. It should be noted that first pump 46 encompasses an outlet line 90 and an inlet line (not shown).

Figure 3:
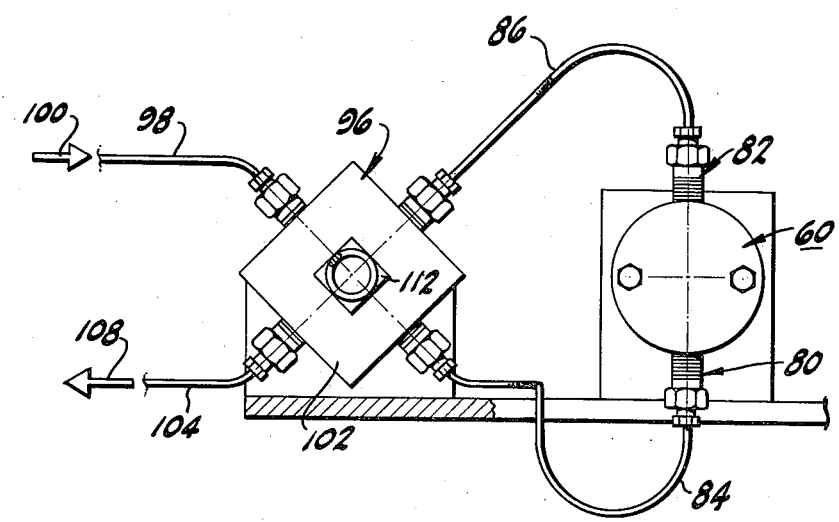
FIG. 3 is a partial sectional view taken along line 3—3 of FIG. 1.
Figure 7:
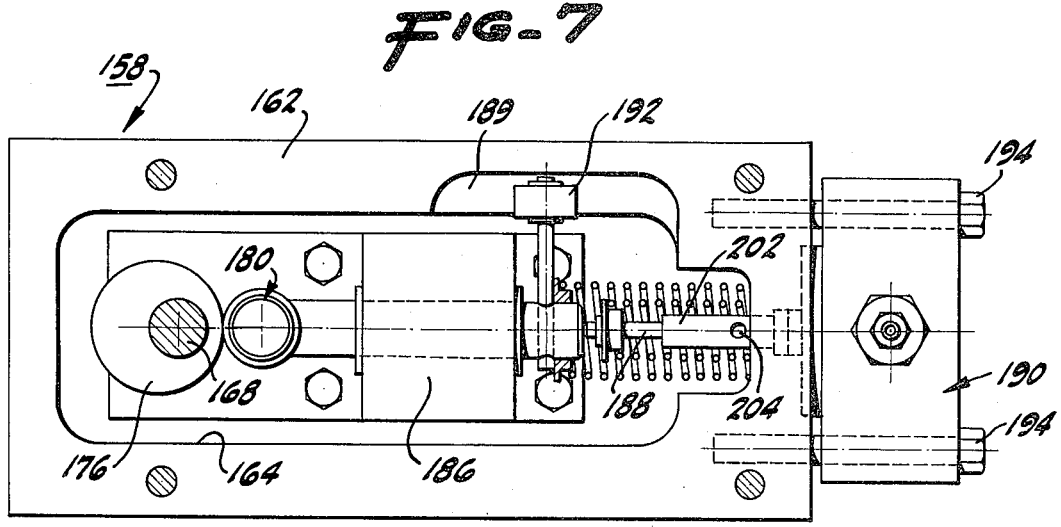
FIG. 7 is a sectional view taken along line 7—7 of FIG. 6.

Shaft 22 operates valve means 92 via cam 38 which is shown on FIG. 1 to include a first valve 94 and a second valve 96. Heretofore described cam followers 40 and 42 are associated with valves 94 and 96 respectively. Again, FIG. 3 depicts second valve 96 which is virtually identical to first valve 94. Valves 94 and 96 are depicted as double, two-way slider valves similar to model number 201-00 manufactured by Altex Scientific, Inc. By way of exemplar, valve 96 functions such that fluids ultimately delivered by pump 48 originate in a fluid reservoir (not shown) and enter inlet tube 98, depicted by directional arrow 100 on FIG. 3. Cam follower 42 operates valve 96 such that fluids pass through valve housing 102 to inlet tube 84 of liquid head 60. At that point, fluid flows through inlet 80 to chamber 64 where piston 62 discharges the same thorugh outlet 82. Since the slider mechanism of valve 96 is well known in the art, the specific functioning thereof will not be described in greater detail. Likewise, fluid exiting outlet 82 of liquid head 60 passes through outlet line 86 through valve housing 102 to exit line 104 (directional arrow 108) which leads to accumulator 106, FIG. 4. The backstroke of piston 62 of pump 48 coincides with the movement of fluid through inlet tube 98 of valve 96 and inlet tube 84 of liquid head 60. Seriatim, the flow of fluid through exit line 104 of valve 96 and exit line 86 of liquid head 60 coincides with the forward stroke, chamber emptying stroke, of piston 62. Returning to FIG. 1, it may be seen that cam followers 42 and 44 actuate the slider mechanisms 110 and 112 of valves 94 and 96 respectively. Return springs 114 and 116 bear on supports 118 and 120 to urge cam followers 40 and 42 into contact with cam 38. It should be further clarified that cam 38 operates valves 94 and 96 such that valve 94 discharges to accumulator 106 while valve 96 sucks fluid from the fluid reservoir, and vice versa. Thus, accumulator 106 received a steady flow of relatively low pressure but very accurately metered fluid, from injector means 12.

Fluid mass accumulating means 106, FIG. 4, receives the fluid delivered by injector means 12 and valve means 92 through inlet port 115 which connects to exit line 104 and another exit line (not shown) of valves 96 and 94. Accumulating means 106 includes a housing 117. Conduit 119 conducts fluid from valve means 92 and delivers the same to chamber 121. A magnetic stirring impeller 122 thoroughly mixes the fluids from injector means 12 and injector means 139 (discussed hereinafter) with the use of dipole stirrer 124. Fluids entering port 115 pass into a portion of connected chamber 126 located above chamber 121, FIG. 4. Chamber 126 is divided into system fluid section 128 and capacitance section 130 by diaphragm 132. Fluid being pumped by injector 12 impinges on diaphragm 132 before entering exit conduit 134 and exit port 136. In general, stirring impeller 122 may be constructed of non-reactive material such as Teflon, Kel-F, and the like. With reference to FIG. 10, another injector means 139 (shown schematically) would deliver another fluid stream to inlet port 138 of fluid mass accumulating means 106. Injector means 139 would be similar in construction to injector means 12. The desired solvent composition or gradient would be determined by the relative flow rates of fluid from injector means 12 and 139. Thus, fluid mass accumulating means 106 could accept a multiplicity of fluid streams for a multiplicity of injector means. Mixing chamber 121 permits the blending of the fluid outputs of injector means 12 and 139, which, in the case of a liquid chromatography gradient, would consist of distinct solvent streams.

FIG. 4 also depicts means 140 for detecting a fluid mass in accumulating means 106. Diaphragm 132 has as one of its elements, a conductive portion 142 which is electrically connected to ground. Diaphragm 132 is held between housing 117 and member 144 by fastening means 146. Detecting means 140 includes a capacitance electrode 148 which is fixed to the under surface of a printed circuit board 150. Circuit components 152 and 154 and connector 156 mount to the top portion of printed circuit board 150, FIG. 5. Full details of the electrical components of the system 10 will be described as the specification continues. However, the impingement of system fluid on flexible diaphragm 132 creates a variable capacitor between conductive portion 142 and capacitance electrode 148. Thus, changes in the mass of fluid present in accumulating means 106 is detected by detecting means 140. As shown in the preferred embodiment, the amount of fluid mass is transduced into a value of capacitance. However, it should be noted that an optical or mechanical mechanism would perform the same function as the capacitor hereinbefore described.

Fluids passing through accumulating means 106 enter high pressure pump means 158, FIGS. 6 through 9. As shown in the preferred embodiment, high pressure pump means 158 is a piston driven diaphragm pump. Other types of high pressure pumps, such as solenoid driven diaphragm pumps, dual piston pumps, and the like may be employed to boost the fluid pressure of the fluid arriving from accumulating means 106. For example, fluid pressure may be boosted from a slightly positive absolute value to over 700 kilograms per square centimeter. Pump means 158 includes a housing 160 having an enclosure 152 which forms chamber 164. Chamber 164 holds lubricating fluids depicted in FIG. 6 as an oil bath 166. A conventional variable speed motor M-10, FIG. 12, turns shaft 168 at a rate determined by control means 242. Shaft 168 is supported by bearing 170 before it passes through an opening 172 in enclosure 162. Seal 174 prevents the escape of oil from chamber 164 while permitting shaft 168 to turn. The end of shaft 168 is supported by needle bearing 174 located within chamber 164. Cam 176 is held to shaft 168 by fastening means 178, thus cam rotates with the turning of shaft 168. Cam follower 180 is illustrated as rollingly engaging the surface of cam 176. Cam follower 180 is fastened to cam follower shaft 182 by fastening means 184. Shaft 182 passes through bearing means 186 and contacts piston 188. Enclosure 162 provides a shelf 189, FIG. 7, which engages guide roller 192. Guide roller 192 prevents the axial turning of cam follower shaft 182.

Figure 8:
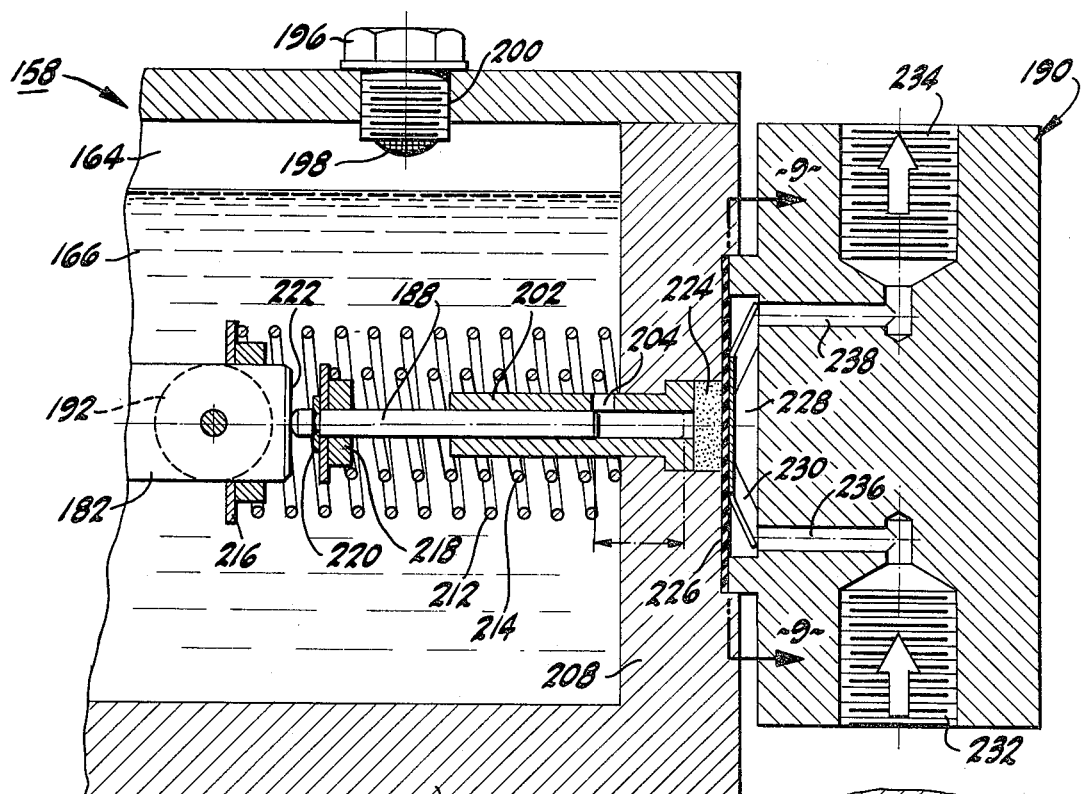
FIG. 8 is an enlarged view of the right-hand portion of the high pressure pump means depicted in FIG. 6.
Figure 9:
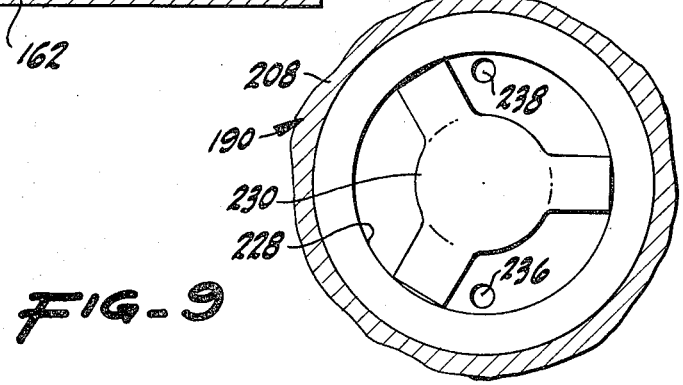
FIG. 9 is a broken view taken along line 9—9 of FIG. 8.

Pump means 158 has as a component liquid head 190 which is bolted onto enclosure 162 by bolt means 194. Turning to FIG. 8, a filler plug 196 having a vent screen 198 occupies replenishment port 200. Thus, the level of oil bath 166 may be easily maintained. Piston 188 moves within guide member 202 in reciprocal fashion. Port 204 insures that piston chamber 206 always contains oil. The stoke of piston 188 is such that the forward pumping stroke extends beyond port 204 to seal the same (shown in phantom) while the backstroke of piston 188 opens port 204. Guide member 202 is held in place by plate 208 which is constructed as part of enclosure 162. Plate 208 also provides a surface 210 for the bearing support of spring members 212 and 214. Spring member 212 insures that contact of cam follower shaft 182 on cam 176. For this purpose cam follower shaft 182 includes a fixed collar 216. In effect, spring member 212 urges cam follower shaft 182 away from surface 210 of plate 208. Similarly, piston 188 includes collar 218 fixed to piston 188 by ring member 220. It may be apparent from the heretofore delineated structure that spring member 214 urges piston 188 into continual contact with end 222 of cam follower shaft 182. Piston chamber 206 terminates at one end thereof, in a relatively rigid member 224, porous to the oil being pumped by piston 188. Adjacent porous member 224 is a relatively flexible diaphragm 226 or membrane which is impervious to the oil pumped. Flexible diaphragm 226 forms one side of fluid chamber 228 within liquid head 190. Diaphragm return spring 230, FIG. 9, wedges into place within chamber 228. Liquid head 190 includes inlet 232 and outlet 234. Inlet 232 accepts fluid leaving exit port 136 of accumulator 106. It should be noted that inlet 232 and outlet 234 include check valves 233 and 235, well known in the art, which insure the flow of fluid shown by the directional arrows in FIG. 8. Fluid entering inlet 232 flows to passage 236 and consequently into fluid chamber 228. At this point the movement of diaphragm 226, actuated by the pumping action of piston 188, constricts the volume of fluid chamber 228 and forces the fluid into passage 238. The fluid then passes from passage 238, through outlet 234, to the desired delivery terminal. In the case of a liquid chromatography system, the outlet flow from outlet 234 would enter a packed column 240, shown schematically on FIG. 10. In the case of check valve failure, porous member 224 would support diaphragm 226 against rupture.

With reference to FIG. 10, the system 10 is shown schematically. Injector means 12, composed of first and second pumps 46 and 48, and valves 94 and 96, and/or similarly constructed injector means 139 deliver fluid to fluid mass accumulating means 106. The combined fluid stream travels to high pressure pump means 158 and column 240 thereafter. Detecting means 140 senses fluid mass in accumulating means 106 and produces a signal representing the detected fluid mass which is then sent to control means 242. Control means 242 compares this signal to reference signal and in turn produces an error signal which regulates the flow rate of high pressure pump means 158. This regulation of high pressure pump means 158 attempts to maintain the mass of fluid contained in accumulator 106 to a reference value. In the embodiment shown in the drawings, the flow rate of high pressure pump means 158 would be controlled by the magnitude of the voltage reaching the motor turning shaft 168. Thus, the flow rate of fluid leaving high pressure pump means equals the flow rate of fluid being delivered by injector means 12 and/or any other injector means. A controller 268 may determine the composition and/or gradient of solvents delivered by any multiplicity of injector means. Sample injection means 270 combines the sample to be analized with the solvent stream leaving high pressure pump means 158.

Figure 11:
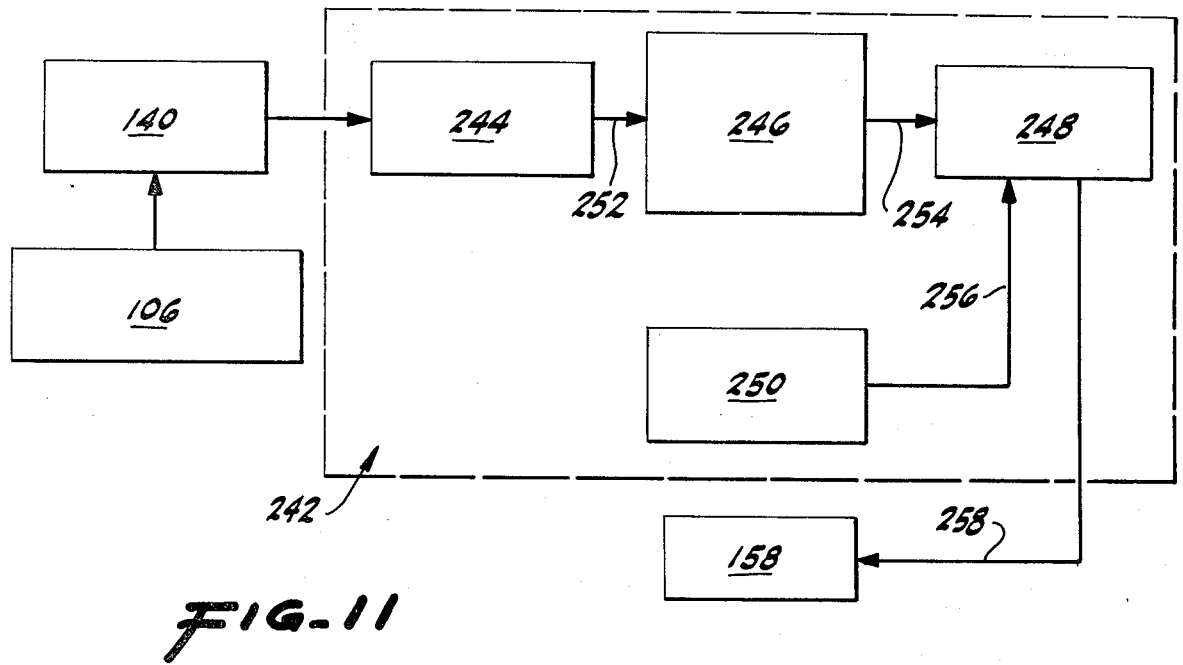
FIG. 11 is a block diagram of booster speed control means.

FIG. 11 further depicts schematically a particular embodiment of control means 242. As heretofore described, the fluid mass signal from detector 140 is received by control means 242 and converted into a signal which regulates the flow rate of high pressure pump means 158. Control means 242 includes an oscillator 244 which generates a frequency signal 252 which is proportional to the inverse of the capacitance between capacitance electrode 148 and conductive portion 142 of diaphragm 132. Frequency signal 252 is transformed into a voltage signal by frequency to voltage converter 246. Voltage signal 253 is received by summing amplifier 248. Reference voltage generator 250 also sends a voltage signal 256 representative of a reference mass value for fluid mass accumulating means 106 to summing amplifier 248 which in turn sends a voltage signal 258 which controls the speed of the motive means associated with high pressure pump means 158. It should be noted that such motive means may be a simple D.C. motor, well known in the art. Thus, an increase in the pumping rate of injector 12 would increase the fluid mass in fluid mass accumulator 106. Detecting means 140 would realize such an increase and signal the same to control means 242 which would increase the pumping rate of high pressure pump means 158. The increase flow rate from high pressure pump means 158 would tend to decrease the mass of fluid found in fluid mass accumulator means 106. The null circuit described hereinbefore with control means 242 essentailly renders high pressure pump means 158 as a slave to injector means 12, and/or 139, the master.

Figure 12:
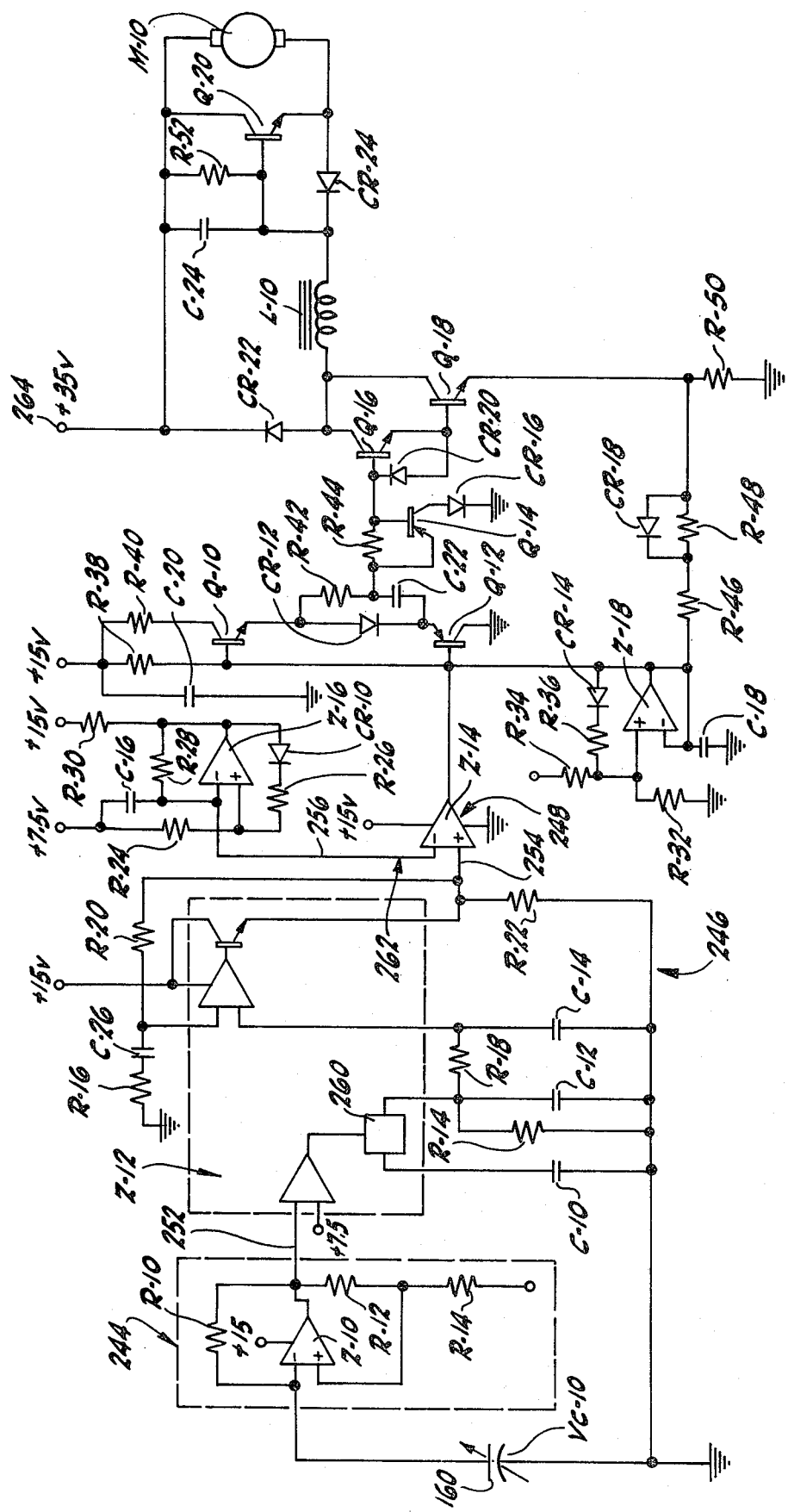
FIG. 12 is an electrical schematic diagram of the pressure booster speed control means.

FIG. 12 represents an embodiment of an electrical circuit which performs the nulling function associated with detecting means 140 and control means 242. The following table is a compilation of values of the components identified on FIG. 12:

TABLE I

| FIG. 12 CIRCUIT ELEMENTS | |
| --- | --- |
| R-10 | 200 K. OHM |
| R-12 | 10 K. OHM |
| R-14 | 100 K. OHM |

TABLE I-continued

| FIG. 12 CIRCUIT ELEMENTS | |
| --- | --- |
| R-16 | 8.2 K. OHM |
| R-18 | 100 K. OHM |
| R-20 | 82 K. OHM |
| R-22 | 10 K. OHM |
| R-24 | 39 K. OHM |
| R-26 | 22 K. OHM |
| R-28 | 30 K. OHM |
| R-30 | 10 K. OHM |
| R-32 | 3.9 K. OHM |
| R-34 | 200 K. OHM |
| R-36 | 47 K. OHM |
| R-38 | 2.2 K. OHM |
| R-40 | 4.7 K. OHM |
| R-42 | 1 K. OHM |
| R-44 | 68 K. OHM |
| R-46 | 470 K. OHM |
| R-48 | 1.5 K. OHM |
| R-50 | 0.3 K. OHM |
| R-52 | 56 K. OHM |
| VC-10 | Range 10–100 p.f. |
| C-10 | 620 p. farads |
| C-12 | 0.02 micro farads |
| C-14 | 0.02 micro farads |
| C-16 | 0.001 micro farads |
| C-18 | 0.01 micro farads |
| C-20 | 15 micro farads |
| C-22 | 0.1 micro farads |
| C-24 | 100 micro farads |
| C-26 | 2.2 micro farads |
| Z-10 | RCA CA-3130 |
| Z-12 | National Semi-conductor LM2907N |
| Z-14¼ | National Semi-conductor LM 339N |
| Z-16¼ | National Semi-conductor LM 339N |
| Z-18¼ | National Semi-conductor LM 339N |
| Q-10 | MPS 6531 |
| Q-12 | MPS 3638A |
| Q-14 | MPS 3638A |
| Q-16 | 2N 5189 |
| Q-18 | RCA 40375 |
| Q-20 | 2N6386 |
| CR-10 | IN914 |
| CR-12 | IN914 |
| CR-14 | IN914 |
| CR-16 | IN914 |
| CR-18 | IN914 |
| CR-20 | IN914 |
| CR-22 | MR850 |
| CR-24 | MR850 |
| L-10 | 300 Micro-henry |
| M-10 | Printed Motors, Inc. Model U-9 |

VC-10 or detecting means 160 serves as a summing node sensor. As shown in FIG. 12, VC-10 is a variable capacitor which is a part of oscillator 244 formed by amplifier Z-10 and resistors R-10, R-12, and R-14. The output signal 252 is a square wave signal which may have a frequency from 1 to 10 kilo-hertz. Frequency signal 252 is received by integrated circuit Z-12 which includes charge pump 260. Integrated circuit Z-12 serves as a portion of frequency to voltage converter 246 which has frequency doubling characteristics. Capacitors C-12 and C-14, and resistors R-14 and R-18, comprises a two pole low pass filter. Signal 254 feeds into integrated circuit Z-14. C-10 determines the size of the charge emitted form the charge pump 260 with each axis crossing of signal 252. R-22 bias the output transistor in the operational amplifier in Z-12. R-16, R-20, and C-26 determine the voltage gain of the operational amplifier portion of Z-12. R-16 and C-26 form a zero which increases the gain of the operational amplifier of Z-12. R-20 aids in this stabilization of the feedback loop. Passive components C-16, R-28, and R-30, R-24, R-26, and CR-10 combine with Z-16, to produce a triangular wave signal 262 with a D.C. offset voltage signal 256, the output of reference voltage generator 250. Z-14 compares signal 254 and signal 262 and 256 to produce a pulse width modulated signal 258 directly proportional to the voltage signal 254. Thus, Z-14 serves as summing amplifier 248.

Q-10, Q-12, Q-14, and Q-16 drive Q-18 synchronously "on" and "off" at a very fast rate. R-38 serves as a pull-up resistor for Z-14 while C-20 filters the power supplied thereto. R-40 functions to limit the peak current through Q-10. Q-10 and Q-12 turn on and off in complimentary sequence. Pulse-width modulated siganl which is quite high and positive pushes current through CR-12. C-22, R-42, R-44, Q-14, and to the base of Q-16.

Q-14 bypasses to ground, through CR-16, any excess current received from Q-10. The current through R-44, which is not bypassed, passes to the base of Q-16 and turns it on. The limiting action of Q-14 prevents Q-16 from being over driven when the system is initially turned on, thus Q-16 can be turned off more quickly. After the charge up of C-22, R-42 limits the drive current through Q-10 such that Q-14 does not bypass measurable current to ground after the charge up period of C-22. The collector of Q-18 reaches a low value after a short time from the beginning of the turn-on sequence. When the pulse width modulated signal goes to a low value, Q-12 turns "on" and Q-10 turns "off" allowing the voltage at the emitter of Q-12 to go to a low value. C-22 supplies a source of negative bias to remove large currents very rapidly from the bases of Q-16 and Q-18 through CR-20. Consequently, Q-16 and Q-18 are turned off very rapidly permitting the voltage on the collectors thereof to go to a high value. This "on-off", high/low sequence takes place at a relatively high frequency thus eliminating the need of a large heat sink to dissipate the heat from Q-18.

The schematic also shows means for current limiting Q-18 using current sensing resitor R-50 and Z-18 and its associated circuitry. Z-18 compares a reference voltage derived from R-32, R-34, and R-36, and the signal voltage developed across C-18. Such a signal voltage averages the voltage drop across the current sensing resistor R-50 with a dual time constant originating from R-46, R-48, and CR-18. For instance, when the voltage drop across R-50 is less than the voltage across C-18, CR-18 is reversed biased so that R-46 and R-48 determine the time constant associated with C-18. When the signal voltage exceeds the reference voltage in comparator Z-18, the output of comparator Z-18 overrides the pulse width modulated signal from Z-14, thereby shutting down the driver section of the circuit. R-36 drops the reference voltage to a low level which guaranties that the driver section will remain in an off position for a set time period. When the signal from C-18 is discharged below the lowered reference signal, Z-14 is again ready to reactivate the driver section of the circuit. The "on-off" action of this current limiting occurs at a predetermined frequency.

L-10 and C-24 combine to produce a low pass filter, which reacts slowly to voltage changes from the driver section of the circuit. By this means the pulse width modulated signal is converted to a D.C. signal supplied to M-10, a D.C. motor driving high pressure pump means 158. R-52, Q-20 and CR-24 form a dynamic brake which prevents the over speeding of M-10. In other words, when CR-24 is forward biased, Q-20 is off and the L-10, CR-22, low pass filter controls M-10. However, if the D.C. voltage generated by motor M-10 exceeds the D.C. supplied across C-24, CR-24 will reverse bias and Q-20 goes "on". This short circuits and therefore brakes M-10. Diode CR-22 clamps the voltage on the collectors of Q-16 and Q-18 to the thirty five (35) volt source 264, when Q-18 is in the "off" position.

Returning to FIG. 1, it may be seen that electrical motor 14 provides the motive force for injector 12. Motor 14 may be a stepping motor such as a Copal, SP 45. Control means 266 determines the selected speed of motor 14 and therefore the selected pumping rate of injector 12. Control means 266 may consist of a drive module such as Copal DM 402X linked to a PG-01 pulse generator. The drive module and pulse generator may be controlled a simple variable resistor or "pot" having about a 500K OHM rating. Thus, the user may set the pot to control the speed of stepping motor 14. Such control may be programmed automatically.

In operation, the user sets the speed of stepping motor 14 via control 266. Thus, a pumping rate for injector 12 is selected and may correspond to a pressure value necessary to push fluid through liquid chromatography column 240. Motor 14 turns shaft 18 which in turn cause pumps 46 and 48 to deliver a carefully metered low pressure fluid in conjunction with valves 94 and 96 to fluid mass accumulating means 106. Fluid passes through accumulator 106 and enters high pressure pump means 158. Fluid mass accumulating means 106 also serves as a node for feedback system which controls the speed of motor M-10, the motive means for high pressure pump means 158. Detecting means 140 and control means 242 comprise a null circuit which results in the proper pumping rate for high pressure pump means 158. The resulting output therefrom, passes to liquid chromatography column 240.

While in the foregoing specification embodiments of the invention have been set forth in considerable detail for the purpose of making a complete disclosure of the invention, it will be apparent to those of ordinary skill in the art that numerous changes may be made in such detail without departing from the spirit and principles of the invention.

What is claimed is:

1. A pressure booster system for fluids comprising:
   a. injector means for delivering a selected relatively low pressure output flow of fluid;
   b. means for accumulating fluid mass from said relatively low pressure injector means, said accumulating means having an output flow;
   c. means for detecting a fluid mass in said fluid mass accumulating means relative to a selected value of fluid mass capable of being confined therein, said detecting means producing a signal representative of said fluid mass in said fluid mass accumulating means;
   d. high pressure pump means for receiving as its input the outlet flow of fluid from said accumulating means and for producing a high pressure output flow of fluid; and
   e. control means for regulating the flow rate of said relatively high pressure pump means according to said fluid mass signal received from said detecting means, said control means comparing said detecting means signal to a reference signal proportionate to said selected value of fluid mass.

2. The pressure booster system for fluids of claim 1 in which said fluid mass accumulating means comprises:
   a fluid container having an inlet, and outlet, and a flexible diaphragm forming a portion of said container.

3. The pressure booster system of claim 2 in which said injector means is first injector means for delivering a selected relatively low pressure output flow of a first fluid and said system further comprises at least a second injector means for delivering a selected relatively low pressure output flow of a second fluid, and said means for accumulating fluid mass accumulates fluid mass from said first and second injector means.

4. The pressure booster system for fluids of claim 2 in which said means for detecting a fluid mass in said fluid mass accumulating means comprises providing means for detecting the position of said flexible diaphragm.

5. The pressure booster system of claim 4 in which said means for detecting the position of said flexible diaphragm comprises means for transducing said detected position of said flexible diaphragm into said signal representing said fluid mass in said fluid mass accumulating means.

6. The pressure booster system for fluids of claim 5 in which said means for detecting the position of said flexible diaphragm comprises an electrically conductive portion therewith movable with said flexible diaphragm, including a capacitance electrode spaced a variable distance from said electrically conductive portion of said flexible diaphragm, and including means for measuring the capacitance generated between said capacitance electrode and said electrically conductive portion of said flexible diaphragm and for generating a signal representative of said capacitance.

7. The pressure booster system for fluids of claim 6 in which said control means for regulating the flow rate of said relatively high pressure pump means comprises:
   a. an oscillator receiving the capacitance signal from said means for measuring capacitance and generating a signal representative thereof and for producing an output frequency signal representative of the capacitance between said capacitance electrode and said electrically conductive portion of said flexible diaphragm;
   b. means for converting said output frequency signal to a voltage signal; and
   c. summing amplifier means for comparing said voltage signal to a reference voltage signal and for producing a voltage from said comparison for motivating said high pressure pump means.

8. The pressure booster system of claim 1 in which said high pressure pump means comprises:
   a. a piston being reciprocative within a first chamber adapted for containing a first fluid;
   b. motive means for reciprocating said piston;
   c. a flexible membrane forming a wall of said first chamber and also forming a wall of a second chamber adapted for containing a second fluid, said flexible diaphragm being movable with the stroke of said piston;
   d. valve means for permitting the filling and emptying of said second chamber coordinated with the movement of said flexible membrane;
   e. spring means for returning said flexible membrane in a direction opposite to the movement of said piston urging said first fluid against said flexible membrane;
   f. a relatively rigid member interposed between said piston and said flexible membrane, said relatively rigid member being porous to said first fluid.

9. The pressure booster system of claim 8 in which said high pressure pump additionally comprises:
   a. a cam rotatable by said motive means;
   b. cam follower being reciprocative by said cam, said cam follower bearing on said piston and imparting reciprocal motion thereto;
   c. first spring means for urging said cam follower into contact with said cam; and
   d. second spring means for urging said piston into contact with said cam follower.

10. The pressure booster system of claim 9 in which said cam follower is an elongated member and said high pressure pump means additionally comprises means for preventing axial rotation of said cam follower.

11. The pressure booster system for fluids of claim 8 in which said fluid mass accumulating means comprises:
    a fluid container having an inlet, and outlet, and a flexible diaphragm forming a portion of said container.

12. The pressure booster system for fluids of claim 11 in which said means for detecting a fluid mass in said fluid mass accumulating means comprises providing means for detecting the position of said flexible diaphragm.

13. The pressure booster of claim 12 in which said means for detecting the position of said flexible diaphragm comprises means for transducing said detected position of said flexible diaphragm into said signal representing said fluid mass in said fluid mass accumulating means.

14. The pressure booster system for fluids of claim 13 in which said means for detecting the position of said flexible diaphragm includes an electrically conductive portion movable with said flexible diaphragm, a capacitance electrode spaced a variable distance from said electrically conductive portion of said flexible diaphragm, means for measuring the capacitance generated between said capacitance electrode and said electrically conductive portion of said flexible diaphragm and means for generating a signal representative of said capacitance.

15. The pressure booster system for fluids of claim 14 in which said control means for regulating the flow rate of said relatively high pressure pump means comprises:
    a. an oscillator receiving the capacitance signal from said means for measuring capacitance and generating a signal representative thereof and for producing an output frequency signal representative of the capacitance between said capacitance electrode and said electrically conductive portion of said flexible diaphragm;
    b. means for converting said output frequency signal to a voltage signal; and
    c. summing amplifier means for comparing said voltage signal to a reference voltage signal and for producing a voltage from said comparison for motivating said high pressure pump means.

16. The pressure booster system of claim 1 in which said injector means comprises:
    a. a shaft;
    b. motive means for turning said shaft at a selected rotational speed;
    c. first reciprocal pump means operated by a first cam fixed to said shaft;
    d. second reciprocal pump means operated by said first cam fixed to said shaft;
    e. a fluid reservoir;
    f. first valve means operated by a second cam fixed to a shaft, said first valve means permitting flow of fluid from said fluid reservoir to said first reciprocal pump means during the intake stroke of said first reciprocal pump means, and permitting discharge of the fluid during the pump-out stroke of said first reciprocal pump means; and g. second valve means operable by said second cam fixed to said shaft, said second valve means permitting flow of fluid from said fluid reservoir to said second reciprocal pump means during the intake stroke of said second reciprocal pump means, and permitting discharge of the fluid during the pump-out stroke of said second reciprocal pump means.

17. The pressure booster system of claim 16 in which said first and second cams of said injector means are positioned on said shaft such that said first and second reciprocal pump means of said injector means are coordinated to pump fluid during separate time intervals.

* * * * *